United States Patent
Iversen et al.

(10) Patent No.: US 11,793,800 B2
(45) Date of Patent: *Oct. 24, 2023

(54) METHODS AND COMPOSITIONS TO INHIBIT ADVERSE EFFECTS ASSOCIATED WITH VACCINATIONS

(71) Applicant: SEN-JAM PHARMACEUTICAL LLC, Huntington, NY (US)

(72) Inventors: Jacqueline M. Iversen, Lloyd Harbor, NY (US); Thomas A. Dahl, Guilford, CT (US)

(73) Assignee: SEN-JAM PHARMACEUTICAL INC., Huntington, NY (US)

( * ) Notice: Subject to any disclaimer, the term of this patent is extended or adjusted under 35 U.S.C. 154(b) by 310 days.

This patent is subject to a terminal disclaimer.

(21) Appl. No.: 17/136,799

(22) Filed: Dec. 29, 2020

(65) Prior Publication Data

US 2021/0113538 A1    Apr. 22, 2021

Related U.S. Application Data

(63) Continuation of application No. 16/113,830, filed on Aug. 27, 2018, now Pat. No. 10,874,653.

(60) Provisional application No. 62/552,029, filed on Aug. 30, 2017.

(51) Int. Cl.
| | | |
|---|---|---|
| *A61K 31/616* | (2006.01) | |
| *A61K 31/445* | (2006.01) | |
| *A61K 31/20* | (2006.01) | |
| *A61P 39/00* | (2006.01) | |
| *A61P 29/00* | (2006.01) | |
| *A61K 31/192* | (2006.01) | |

(52) U.S. Cl.
CPC .......... *A61K 31/445* (2013.01); *A61K 31/192* (2013.01); *A61P 29/00* (2018.01); *A61P 39/00* (2018.01)

(58) Field of Classification Search
CPC ..... A61K 31/616; A61K 31/445; A61K 31/20
USPC ........................................ 514/165, 317, 559
See application file for complete search history.

(56) References Cited

U.S. PATENT DOCUMENTS

| | | |
|---|---|---|
| 10,420,756 B2 | 9/2019 | Iversen et al. |
| 10,675,261 B2 | 6/2020 | Iversen et al. |
| 10,765,630 B2 | 9/2020 | Iversen et al. |
| 10,874,653 B2 * | 12/2020 | Iversen .................. A61P 39/00 |
| 11,129,803 B2 | 9/2021 | Iversen et al. |
| 11,464,766 B2 | 10/2022 | Iversen et al. |
| 2005/0158329 A1 | 7/2005 | Ghosh |
| 2015/0182564 A1 | 7/2015 | Wolfenden |
| 2016/0279112 A1 | 9/2016 | Iversen et al. |
| 2016/0310588 A1 | 10/2016 | Cun et al. |
| 2018/0360811 A1 | 12/2018 | Iversen et al. |
| 2019/0083430 A1 | 3/2019 | Iversen et al. |

FOREIGN PATENT DOCUMENTS

WO    WO 2022032069 A1    2/2022

OTHER PUBLICATIONS

"Clinical Guidelines for Managing Adverse Effects after Vaccination", US Army Medical Command, Aug. 2002, pp. 1-26; https://biotech.law.lsu.edu/biaw/bt/smallpox/mil/cpguidelines.pdf.

"Antihistamines and child vaccination; Preparation for vaccination"; New York blog (http://webuserblog.com); Aug. 5, 2015 (http://webuserblog.com/?M=20150805); New York Tips (http://webuserblog.com/?CAT=201); New York Tips http://webuserblog.com/?CA T =373).

Susan Nelson, DVM, Kansas State University, Veterinary Health Center, Pet Health Center, "Vaccinations"; https://www_vet.k-state.edu/vhc/services/phc/vaccinations.html; Updated Mar. 30, 2017.

Erin Ryder; "Injection Objection: Adverse Vaccine Reactions"; Mar. 4, 2014; http://www.thehorse.com/articles/16770/injection-objection-adverse-vac . . . ; The Horse, Your Guide to Equine Health Care.

Pickens Animal Hospital; Vaccination FAQ.

Richard B. Ford, DVM, MS; North Carolina State University; "Post-Vaccinal Adverse Events"; Kentucky Veterinary Medical Association; Updated Jan. 2012.

Tricia Kinman; "Flu Shot: Learn the Side Effects"; Medically Reviewed by Philip Gregory, PharmD, MS on Nov. 7, 2016; Healthline, http://www.healthline.com/health/flu-shot-side-effects?m=O&print=true.

Barbara Robb; "Vaccine Allergy: A Closer Look"; Medically Reviewed by Christine Wilmsen Craig, MD; Everyday Health Media, LLC; Last Updated: Feb. 1, 2013; http://www.everydayhealth.com/allergies/vaccine-allergy.aspx.

Heather Smith Thomas; "Tips to Prevent or Minimize Vaccination Reactions"; EquiMed-Horse Health Matters; Aug. 5, 2014; http://equimed.com/health-centers/general-care/articles/tips-to-prevent-or . . . .

Michelle K. Pesce, DVM; Worried About Vaccine Reactions?; Bolton Veterinary Hospital; Feb. 20, 2014; http://www_boltonvet.com/?p=497.

Ron Hines DVM PhD; "Preventing Anaphylaxis-Acute Allergic Shock In Dogs, Cats And Ferrets—Vaccine Reactions"; Jnd Chance; http://www.2ndchance.info/anaphylaxis.htm.

* cited by examiner

*Primary Examiner* — Raymond J Henley, III
(74) *Attorney, Agent, or Firm* — Morgan, Lewis & Bockius LLP

(57) ABSTRACT

The invention relates to methods of inhibiting side effects associated with vaccination in a human subject in need thereof. The method comprises administering an effective amount of a pharmaceutical composition to the subject before the subject is vaccinated, wherein the pharmaceutical composition comprises: a) a non-steroidal anti-inflammatory drug (NSAID); and b) a co-agent selected from the group consisting of: fexofenadine, ketotifen, desloratadine and cetirizine and combinations thereof.

14 Claims, No Drawings

METHODS AND COMPOSITIONS TO INHIBIT ADVERSE EFFECTS ASSOCIATED WITH VACCINATIONS

CROSS REFERENCE TO RELATED APPLICATIONS

This application is a continuation of U.S. patent application Ser. No. 16/113,830, filed on Aug. 27, 2018, which claims the benefit of U.S. Provisional Application Ser. No. 62/552,029 filed Aug. 30, 2017, which are incorporated herein by reference in their entirety.

FIELD OF THE INVENTION

The present invention relates to methods, and compositions, for inhibiting adverse side effects associated with administration of vaccinations.

BACKGROUND OF THE INVENTION

Infectious diseases such as, for example, small pox, measles and yellow fever, can be deadly. In some cases, even influenza virus infections can be severe, even life-threatening, especially in young children, older adults, individuals with underlying health conditions, and pregnant women. According to the Centers for Disease Control and Prevention (CDC), approximately two hundred thousand people are hospitalized yearly due to influenza.

Vaccination can prevent or ameliorate infectious disease. Vaccination is the administration of antigenic material (a vaccine) to stimulate an individual's immune system to develop adaptive immunity to a pathogen. The adaptive immune system is one of the two main immunity strategies found in vertebrates (the other being the innate immune system). The adaptive immune system is composed of highly specialized, systemic cells and processes that eliminate pathogens or prevent their growth. That is, after an initial response to a specific pathogen, the adaptive immunity creates immunological memory, and leads to an enhanced response to subsequent encounters with that pathogen, providing long-lasting protection. This process of acquired immunity is the basis of vaccination.

The effectiveness of vaccination has been widely studied and verified (e.g., Fiore et al., "Seasonal influenza vaccines." Current Topics in Microbiology and Immunology. 333:43-82 (2009)). Vaccination is found to be the most effective method of preventing infectious diseases; widespread immunity due to vaccination is largely responsible for the worldwide eradication of smallpox and the elimination of diseases such as polio, measles, and tetanus from much of the world. The World Health Organization (WHO) reports that licensed vaccines are currently available for twenty-five different preventable infections.

Accordingly, it is critical to protect against contracting infectious diseases, including the influenza virus, by the administration of vaccines. However, many are discouraged from obtaining vaccinations due to a variety of undesirable side effects associated with vaccines, ranging from mild to severe. For example, according to the Centers for Disease Control, mild side effects from the influenza vaccine include soreness, redness or swelling at the injection site; low-grade fever; and aches. The 2015-2016 influenza vaccine for U.S. administration reported an incidence of injection site pain of 50% and an incidence of flu-like symptoms of 15-20% (Fluarix Quadrivalent Package Insert 2015. GlaxoSmithKline, Research Triangle Park, N.C.). For children, some side effects from the flu nasal spray can include runny nose, wheezing, headache, vomiting, muscle aches and fever. For adults, side effects include runny nose, headache, sore throat and cough. Rare but serious side effects can also occur, including allergic reactions. In many cases, the fear of having side effects due to vaccinations discourages individuals from obtaining vaccinations.

Due to the potential consequences of contracting infectious diseases, and the efficacy of most vaccinations, there is a need to encourage the widespread administration of vaccinations. Accordingly, there is a need to reduce the side effects associated with vaccinations.

SUMMARY OF THE INVENTION

In one embodiment, the present invention relates to a method of inhibiting side effects associated with vaccination in a human subject in need thereof, comprising: administering an effective amount of a pharmaceutical composition to the subject before the subject is vaccinated. The pharmaceutical composition comprises: a) a non-steroidal anti-inflammatory drug (NSAID); and b) a co-agent selected from the group consisting of: fexofenadine, ketotifen, desloratadine and cetirizine and combinations thereof. Examples of NSAIDs include aspirin, ibuprofen, naproxen, diclofenac, diflunisal, etodolac, indomethacin, ketoprofen, ketorolac, meloxicam, nabumetone, oxaprozin, piroxicam, salsalate, sulindac, tolmetin and their salts. In one embodiment the NSAID is naproxen sodium and the co-agent is fexofenadine, e.g., about 220 mg to about 880 mg of naproxen sodium, and about 60 mg to about 180 mg of fexofenadine. In one embodiment, the naproxen sodium and the fexofenadine are combined into one unit dose. The naproxen sodium and the fexofenadine can be in the form of a tablet, lozenge or chewing gum. In one embodiment, the pharmaceutical composition is administered daily beginning at most 24 hours before administration of a vaccine. In one embodiment, the vaccine is an influenza vaccine. In one embodiment, the inhibited side effects include injection site soreness, congestion, cough, fever, and/or muscle/joint pain. Examples of the amount of ibuprofen is about 200 mg to about 800 mg, of the amount of aspirin is about 325 mg to about 1000 mg, of the amount of ketotifen is about 0.5 mg to about 3 mg, of the amount of desloratidine is about 5 mg to about 10 mg, of the amount of cetirizine is about 2 mg to about 10 mg.

In another embodiment, the present invention provides a pharmaceutical composition comprising a) an NSAID, and/or a salt thereof; and b) a co-agent selected from the group consisting of: fexofenadine, ketotifen, desloratadine, cetirizine, salts thereof and combinations thereof. In one embodiment, the composition is in the form of an orally-dissolving tablet or lozenge. In one embodiment, the NSAID is selected from the group consisting of: aspirin, ibuprofen, naproxen, diclofenac, diflunisal, etodolac, indomethacin, ketoprofen, ketorolac, meloxicam, nabumetone, oxaprozin, piroxicam, salsalate, sulindac, and tolmetin. In one embodiment, the NSAID is naproxen sodium and the co-agent is fexofenadine, e.g., about 110 mg to about 900 mg of naproxen sodium and about 25 mg to about 200 mg of fexofenadine.

In another embodiment, the present invention provides a method of inhibiting side effects associated with vaccination in a human subject in need thereof, comprising: administering an effective amount of a pharmaceutical composition to the subject within about 48 after the subject is vaccinated. The pharmaceutical composition comprises: a) a non-steroidal anti-inflammatory drug (NSAID); and b) a co-agent selected from the group consisting of: fexofenadine, ketotifen, desloratadine, cetirizine and combinations thereof.

DETAILED DESCRIPTION OF THE INVENTION

In one embodiment, the present invention is directed to methods of inhibiting the adverse side effects associated with vaccinations (e.g., the influenza vaccination) in subjects who were administered such vaccinations. The methods include the administration of particular pharmaceutical compositions.

Throughout this specification, quantities are defined by ranges, and by lower and upper boundaries of ranges. Each lower boundary can be combined with each upper boundary to define a range. The lower and upper boundaries should each be taken as a separate element.

The pharmaceutical compositions of the present invention are effective for use with any type of vaccine, e.g., live, attenuated vaccines; inactivated vaccines; subunit vaccines; toxoid vaccines; conjugate vaccines; DNA vaccines; and recombinant vector vaccines. Additionally, the pharmaceutical compositions of the present invention are effective for use with vaccinations for any type of infectious pathogen, including, for example, influenza, cholera, dengue, diphtheria, hepatitis A, hepatitis B, hepatitis E, *Haemophilus influenzae* type b (Hib), human papillomavirus (HPV), Japanese encephalitis, malaria, measles, meningococcal meningitis, mumps, pertussis, pneumococcal disease, poliomyelitis, rabies, rotavirus, rubella, tetanus, tick-borne encephalitis, tuberculosis, typhoid, varicella and yellow fever.

The pharmaceutical composition comprises a) at least one non-steroidal anti-inflammatory drug ("NSAID"), and b) at least one co-agent.

The NSAID of the present invention includes any NSAID and salts thereof. Examples of suitable NSAIDs include, but are not limited to, aspirin (i.e., acetylsalicylic acid); ibuprofen (i.e., isobutylphenylpropanoic acid); naproxen (i.e., 6-methoxy-α-methyl-2-naphthaleneacetic acid); diclofenac (i.e., 2-[(2,6-dichlorophenyl)-amino]benzene acetic acid); diflunisal (i.e., 2',4'-difluoro-4-hydroxybiphenyl-3-carboxylic acid); etodolac (i.e., (RS)-2-(1,8-diethyl-4,9-dihydro-3H-pyrano[3,4-b]indol-1-yl)acetic acid); indomethacin (i.e., 2-{1-[(4-chlorophenyl)-carbonyl]-5-methoxy-2-methyl-1H-indol-3-yl}acetic acid); ketoprofen (i.e., 3-benzoyl-α-methyl-benzeneacetic acid); ketorolac (i.e., 2-amino-2-(hydroxymethyl)-1,3-propanediol); meloxicam (i.e., 4-hydroxy-2-methyl-N-(5-methyl-2-thiazolyl)-2H-1,2-benzothiazine-3-carboxamide-1,1-dioxide); nabumetone (i.e., 4-(6-methoxy-2-naphthyl)-2-butanone); oxaprozin (i.e., 3-(4,5-diphenyl-1,3-oxazol-2-yl)propanoic acid); piroxicam (i.e., 4-hydroxy-2-methyl-N-2-pyridinyl-2H-1,2-benzothiazine-3-carboxamide 1,1-dioxide); salsalate (i.e., 2-(2-hydroxybenzoyl)-oxybenzoic acid); sulindac (i.e., {(1Z)-5-fluoro-2-methyl-1-[4-(methylsulfinyl)-benzylidene]-1H-indene-3-yl}acetic acid); and tolmetin (i.e., [1-methyl-5-(4-methylbenzoyl)-1H-pyrrol-2-yl]acetic acid).

Suitable co-agents include desloratadine (i.e., 8-chloro-6,11-dihydro-11-(4-piperdinylidene)-5H-benzo[5,6]cyclohepta[1,2-b]pyridine); fexofenadine (i.e., (±)-4-[1 hydroxy-4-[4-(hydroxydiphenylmethyl)-1-piperidinyl]-butyl]-α,α-dimethyl benzeneacetic acid); ketotifen; cetirizine; and salts of such co-agents.

The NSAIDs and co-agents include all pharmaceutically acceptable versions of the NSAIDs and co-agents, including, for example, stereoisomers and/or any mixtures thereof, all pharmaceutically acceptable zwitterions and/or any mixtures thereof, all pharmaceutically acceptable polymorphic forms and/or any mixtures thereof, and all pharmaceutically acceptable complexes (including solvates) and/or any mixtures thereof.

Salts include all salts of NSAIDs and of co-agents which are pharmaceutically acceptable (i.e., non-toxic at therapeutically effective doses). And, salts include their racemates, enantiomers, or any mixtures thereof.

Particularly suitable salts of the NSAIDs comprise alkali-metal salts (e.g., sodium and/or potassium salts), alkaline earth metal salts (e.g., magnesium and/or calcium salts), aluminum salts, ammonium salts, salts of suitable organic bases (e.g., salts of alkylamines and/or -methyl-D-glutamine), salts of amino acids (e.g., salts of arginine and/or lysine). The NSAID salts also include all enantiomeric salts formed with pharmaceutically acceptable chiral acids and/or bases and/or any mixtures of enantiomers of such salts (e.g., (+) tartrates, (−) tartrates and/or any mixtures thereof including racemic mixtures). For example, a typical salt of an NSAID is naproxen sodium.

Examples of suitable salts of the co-agents include ketotifen fumarate, fexofenadine hydrochloride and cetirizine hydrochloride.

Undesirable side effects typically appear shortly after a vaccination. Typical side effects include, for example, substantial physical and mental fatigue; drowsiness; nausea; loss of appetite; cough; runny nose; soreness, redness or swelling at the injection site; low-grade fever; wheezing; headache; vomiting; sore throat; cough; aches (e.g., body aches); inflammation; dizziness; fainting; sneezing; otitis; rhinitis; rhinorrhea; sinusitis; coryza; itchy and watery eyes; malaise; chills; muscle/joint pain; and the like. Rare but serious side effects can occur, including allergic reactions. Signs of serious side effects include difficulty breathing, swelling around the eyes or lips, hives, racing heart and dizziness.

The methods of the present invention comprise the administration of the pharmaceutical composition to a human subject, in need thereof, in an amount which is effective to inhibit the undesirable side effects associated with a vaccination.

In one embodiment, a human subject in need thereof is a subject who is to be vaccinated within about 24 hours. In this embodiment, the pharmaceutical composition is administered to the human subject, in need thereof, before vaccination. For example, administration is at most about one day before vaccination, at most about 12 hours before vaccination, at most about 6 hours before vaccination, at most about 3 hours before vaccination, at most about 2 hours before vaccination, at most about one hour before vaccination, right before vaccination, or essentially simultaneously with vaccination. After the initial dose of the pharmaceutical composition, the pharmaceutical composition can be administered with subsequent doses for no greater than about 2 days.

In another embodiment, a human subject in need thereof is a subject who has been vaccinated within about the past 48 hours. In this embodiment, the pharmaceutical composition is administered to the human subject, in need thereof, after vaccination. For example, administration is right after vaccination, at most about 1 hour after vaccination, at most about 2 hours after vaccination, at most about 6 hours after vaccination, at most about 10 hours after vaccination, at most about 12 hours after vaccination, or about a day after vaccination. After the initial dose of the pharmaceutical composition, the pharmaceutical composition can be administered with subsequent doses for no greater than about 2 days.

In the present specification, the term "inhibit" includes "reduce" and/or "prevent" and/or "shorten duration." That is, the method of the present invention is considered to be effective if it causes one or more of: a reduction/prevention of any undesirable side effect associated with the administration of a vaccine and/or shortening of the duration of an episode of any such undesirable side effect.

Inhibition of undesirable side effects can be assessed by comparing the magnitude and/or duration of at least one side effect in a subject at two different occasions, that is, i) when administered the pharmaceutical composition, and then the subject is administered a vaccine (e.g., an influenza vaccine); and ii) when not administered the pharmaceutical composition, and then the subject is administered the same type of vaccine at a different time (e.g., another influenza vaccine a year later). Inhibition of undesirable side effects can also be assessed by comparing the magnitude and/or duration of at least one side effect in subjects administered the same vaccine, some of whom are administered the pharmaceutical composition and some of whom are not administered the pharmaceutical composition.

Typically, undesirable side effects associated with a vaccination are inhibited by at least about 10%, at least about 20%, at least about 30%, at least about 40%, at least about 50%, at least about 60%, at least about 70%, at least about 80%, at least about 90%, or at least about 100%.

It has unexpectedly been found that the components of the compositions of the present invention have a synergistic effect when inhibiting the undesirable side effects associated with the administration of a vaccine. For example, taking an NSAID is associated with adverse gastrointestinal effects (e.g., upset stomach, ulcers). However, when the NSAIDs of the present invention are taken in combination with the co-agents, they have surprisingly been found to decrease or avoid adverse gastrointestinal effects.

It has been suggested in the art that administration of NSAIDs may reduce the efficacy of vaccines ("Ibuprofen and other widely used non-steroidal anti-inflammatory drugs inhibit antibody production in human cells," *Cell Immunol.* 2009; 258(1):18-28). However, when an NSAID is administered along with a co-agent of the present invention according to the indicated time frame, surprisingly such reduction in the efficacy of vaccines does not occur. Without wanting to be bound by a mechanism, it is believed that by the indicated time frame for administration of the pharmaceutical composition, although the innate immune may be inhibited, the adaptive immune response is not affected thereby allowing a vaccination to be effective. Like the innate system, the adaptive system includes both humoral immunity components and cell-mediated immunity components. Unlike the innate immune system, the adaptive immune system is highly specific to a particular pathogen.

The actual preferred amounts of pharmaceutical composition in a specified case will vary according to the particular compositions formulated, the mode of application, the particular sites of application, and the subject being treated (e.g., age, gender, size, tolerance to drug, etc.).

Examples of typical daily amounts of NSAIDs to be administered in the methods of the present invention follows. The daily amounts can be administered in one dose, or in multiple doses, typically, two doses.

Naproxen from about 150 mg to about 900 mg: Examples of other lower boundaries of this range include about 220 mg, about 275 mg, about 320 mg and about 420 mg. Examples of other upper boundaries of this range include about 580 mg, about 680 mg, about 780 mg and about 880 mg. Other suitable amounts of naproxen include from about 100 mg to about 950 mg.

Ibuprofen from about 150 mg to about 900 mg: Examples of other lower boundaries of this range include about 200 mg, about 220 mg, about 320 mg and about 420 mg. Examples of other upper boundaries of this range include about 580 mg, about 680 mg, about 780 mg and about 800 mg. Other suitable amounts of ibuprofen include from about 100 mg to about 950 mg.

Aspirin from about 250 mg to about 1200 mg: Examples of other lower boundaries of this range include about 325 mg, about 450 mg, about 550 mg and about 650 mg. Examples of other upper boundaries of this range include about 750 mg, about 850 mg, about 950 mg, and about 1000 mg.

Examples of typical daily amounts of the co-agent to be administered in the methods of the present invention follows. The daily amounts can be administered in one dose, or in multiple doses, typically, two doses.

Fexofenadine from about 25 mg to about 200 mg: Examples of other lower boundaries of this range include about 60 mg, about 70 mg, about 80 mg and about 90 mg. Examples of other upper boundaries of this range include about 100 mg, about 120 mg, about 150 mg and about 180 mg. Ketotifen from about 0.5 mg to about 3 mg: Examples of other lower boundaries of this range include about 1 mg, about 1.5 mg and about 1.8 mg. Examples of other upper boundaries of this range include about 2 mg, about 2.5 mg and about 2.8 mg. Desloratidine from about 2 mg to about 10 mg: Examples of other lower boundaries of this range include about 5 mg, about 6 mg and about 7 mg. Examples of other upper boundaries of this range include about 8 mg, about 9 mg and about 10 mg. Cetirizine from about 2 mg to about 10 mg: Examples of other lower boundaries of this range include about 5 mg, about 6 mg and about 7 mg. Examples of other upper boundaries of this range include about 8 mg, about 9 mg and about 10 mg.

In one embodiment of the invention, the pharmaceutical composition of 220 mg naproxen and 60 mg fexofenadine is administered every twelve hours the day before administration of a vaccination, e.g., every twelve hours starting the day before administration.

The pharmaceutical composition can be administered by methods known in the art. For example, the pharmaceutical composition can be administered systemically. For the purposes of this specification, "systemic administration" means administration to a human by a method that causes the compositions to be absorbed into the bloodstream.

In one embodiment, the pharmaceutical compositions are administered orally by any method known in the art. For example, the compositions can be administered in the form of tablets, including, e.g., orally-dissolvable tablets, chewable tablets; capsules; lozenges; pills (e.g., pastilles, dragees); troches; elixirs; suspensions; syrups; wafers; chewing gum; strips; films (e.g., orally-dissolving thin films); soluble powders; effervescent compositions; and the like.

The NSAID and the co-agent can be supplied in combination as one unit dose, or can be supplied individually, e.g., supplied in a package with a unit dose of NSAID and a unit dose of the co-agent.

Additionally, the pharmaceutical compositions can be administered enterally or parenterally, e.g., intravenously; intramuscularly; subcutaneously, as injectable solutions or suspensions; intraperitoneally; sublingually; or rectally (e.g., by suppositories). Administration can also be intranasally, in the form of, for example, an intranasal spray; or transdermally, in the form of, for example, a patch.

The pharmaceutical composition compounds of the invention can be formulated per se in pharmaceutical preparations, optionally, with a suitable pharmaceutical carrier (vehicle) or excipient, as understood by practitioners in the art. These preparations can be made according to conventional chemical methods.

In the case of tablets for oral use, carriers commonly used include lactose and corn starch, and lubricating agents such as magnesium stearate are commonly added. For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums and glycols.

When aqueous suspensions are used for oral administration, emulsifying and/or suspending agents are commonly added. In addition, sweetening and/or flavoring agents may be added to the oral compositions.

For intramuscular, intraperitoneal, subcutaneous and intravenous use, sterile solutions of the pharmaceutically compositions can be employed, and the pH of the solutions can be suitably adjusted and buffered. For intravenous use, the total concentration of the solute(s) can be controlled in order to render the preparation isotonic.

A preferred embodiment of the invention is an orally dissolving tablet comprising an NSAID and a coagent with or without a taste masking ingredient, diluents, etc. Such tablet can be administered without water onto the tongue leading to immediate dissolution and is absorbed gastrointestinally or buccally. Orally dissolving tablets can be formulated by a number of techniques including compression and lyophilization, as would be known to a skilled artisan.

Another preferred embodiment of the invention is a lozenge or troche comprising an NSAID and a co-agent with or without a taste masking ingredient, diluents, etc. Such lozenge/troche can be administered without water, and can slowly dissolve in the mouth, or can be swallowed or chewed. Such lozenges/troches can be formulated by compression, as would be known to a skilled artisan.

The pharmaceutical compositions of the present invention can further comprise one or more pharmaceutically acceptable additional ingredient(s) such as alum, stabilizers, buffers, coloring agents, flavoring agents, and the like. In some embodiments, orally administered pharmaceutical compositions can contain breathe neutralizers, e.g., peppermint or menthol scents.

The pharmaceutical composition may be administered by controlled release. Controlled release administration is a method of drug delivery to achieve a certain level of the drug over a particular period of time. The level typically is measured by plasma concentration. Methods for controlled release of drugs are well known in the art.

The pharmaceutical compositions can be formulated for controlled release. For example, in one embodiment, the composition can be a capsule containing beadlets, wherein some of the beadlets dissolve instantaneously and some of the beadlets dissolve at delayed times due to different types of beadlet coatings.

In one embodiment, the pharmaceutical composition comprises an active ingredient, wherein the active ingredient consists of: a) NSAID, and/or salts thereof, and b) a co-agent selected from the group consisting of: fexofenadine, ketotifen, desloratadine, cetirizine, and/or salts thereof.

In one embodiment, the pharmaceutical composition consists of: a) NSAID, and/or salt thereof, b) a co-agent selected from the group consisting of: fexofenadine, ketotifen, desloratadine, cetirizine, and/or salts thereof; and c) at least one carrier and/or excipient.

In one embodiment, the pharmaceutical composition consists essentially of the active ingredients of: a) NSAID and/or salts thereof, and b) a co-agent selected from the group consisting of: fexofenadine, ketotifen, desloratadine, cetirizine, and/or salts thereof. That is, any other ingredients that may materially affect the basic and novel characteristics of the active ingredients of the invention are specifically excluded from the composition. Any ingredient which can potentially cause an undesirable effect/side effect, including, for example, an allergic response, may materially affect the basic and novel characteristics of the active ingredients of the invention.

The following are some examples of components which may materially affect the basic and novel characteristics of the active ingredients of the pharmaceutical compositions and may be excluded from certain embodiments of the present invention: cyclooxygenase-2-selective inhibitors (i.e., COX-2-selective inhibitors) or prodrugs thereof; sedating antihistamines (e.g., diphenhydramine); decongestants; flunixin meglumine (i.e., banamine); cough suppressants (e.g., guaifenesin, dextromethorphan); $H_2$ antihistamines; ginsenoside; and corticosteroids.

The aforementioned ingredients may materially change the characteristics of the present pharmaceutical composition due to unwanted effects and/or potential allergic responses.

Examples of unwanted potential effects of COX-2-selective inhibitors, or prodrugs thereof, include an increased risk in the incidence of myocardial infarctions. COX-2-selective inhibitors are compounds which selectively inhibit cyclooxygenase-2 over cyclooxygenase-1, and also include pharmaceutically acceptable salts of such compounds, and prodrugs of such compounds. A COX-2 selective inhibitor is any inhibitor for which the ratio of COX-1 $IC_{50}$ to COX-2 $IC_{50}$ is greater than 1. Examples of unwanted potential effects of sedating antihistamines and decongestants include sleepiness, fatigue, dizziness, headache, dry mouth, difficulty urinating or an enlarged prostate and allergic reactions. Examples of unwanted potential effects of flunixin meglumine include ataxia, incoordination, hyperventilation, hysteria and muscle weakness. Examples of unwanted potential effects of guaifenesin include diarrhea, dizziness, headache, hives, nausea or vomiting, skin rash and stomach pain. Examples of unwanted potential effects of dextromethorphan include confusion, constipation, dizziness, drowsiness, headache, nausea or vomiting and stomach pain. Examples of unwanted potential effects of $H_2$ antihistamines include abdominal pain, bleeding or crusting sores on lips, dizziness, fainting, fever and chills. Examples of unwanted potential effects of corticosteroids include fluid retention, edema, weight gain, high blood pressure, headache and muscle weakness.

EXAMPLES

The following examples demonstrate that adverse side effects associated with the administration of influenza vaccinations are inhibited when using the methods of the present invention. JMI-001 is 220 mg naproxen combined with 60 mg fexofenadine. In each of the following examples, JMI-001 (one dose) was administered 1-2 hours before an intramuscular injection of 0.5 ml of an influenza vaccine into the deltoid muscle of an adult. In some cases, a second single dose of JMI-001 was administered 8-10 hours following the injection. Flu-like symptoms (e.g., fever, headache, chills, muscle aches) were measured using a visual analog pain scale 0-10, where 10 is the highest level of flu-like symptoms.

Example 1

A 53 yo healthy female self-administered JMI-001 about 2 hours prior to influenza vaccine injection to the left deltoid muscle. Two hours after vaccination, injection site pain was less than 1 on a pain scale of 0-10. Another dose of JMI-001 was self-administered about 10 hours after vaccine injection. No flu-like symptoms occurred.

Example 2

A 59 yo healthy female self-administered JMI-001 about 2 hours prior to an influenza vaccine injection to the left deltoid muscle. Two hours after vaccination, injection site pain was less than 1 on a pain scale of 0-10. Another dose of JMI-001 was self-administered about 10 hours after vaccine injection. No flu-like symptoms occurred.

Example 3

A 53 yo healthy male self-administered JMI-001 about 2 hours prior to influenza vaccine injection to the left deltoid muscle. Two hours after vaccination, injection site pain was less than 1 on a pain scale of 0-10. Another dose of JMI-001 was not administered and volunteer did not experience flu-like symptoms.

Example 4

A 29 yo healthy male self-administered JMI-001 about two hours prior to an influenza vaccine injection to the left deltoid muscle. Two hours after vaccination, injection site pain was less than 1 on a pain scale of 0-10. Another dose of JMI-001 was self-administered about 10 hours after vaccine injection. No flu-like symptoms occurred.

Example 5

A 56 yo healthy male received a number of vaccinations prior to a planned trip to Africa. On day 1, he received 2 intramuscular injections (one each of influenza vaccine and Tdap) while also receiving 3 subcutaneous injections (one each of MMR, yellow fever and cholera vaccine). In addition, he self-administered a total of 4 doses of oral vaccine against typhoid on days 1, 3, 5 and 7. Four hours prior to receiving the vaccinations on day 1, he self-administered fexofenadine 180 mg with naproxen sodium 220 mg and self-administered this same combination at 6 hours after the vaccinations and every 12 hours thereafter until the end of day 2, and did not experience any injection site pain, only slight bruising and no flu-like symptoms. When he self-administered his second dose of typhoid oral vaccination on day 3 he had not taken the oral naproxen sodium 220 mg and fexofenadine 180 mg since 12 hours prior. He did not experience any flu-like symptoms. He decided to continue without the combination of fexofenadine and naproxen even when he self-administered the third dose of typhoid oral vaccination on day 5. A few hours after self-administering the third dose of oral typhoid vaccination, he experienced headache, muscle weakness and other flu-like symptoms including nausea for which he began taking the combination of fexofenadine 180 mg with naproxen sodium 220 mg at that time and every 12 hours thereafter. His pain and flu-like symptoms subsided within 4 hours. He then self-administered his fourth and last dose of oral typhoid vaccination on day 7, while continuing with the fexofenadine 180 mg and naproxen sodium 220 mg every 12 hours and did not experience any flu-like symptoms from the oral vaccine.

Thus, while there have been described what are presently believed to be the preferred embodiments of the present invention, other and further embodiments, modifications, and improvements will be known to those skilled in the art, and it is intended to include all such further embodiments, modifications, and improvements as come within the true scope of the claims as set forth below.

The invention claimed is:

1. A method of inhibiting side effects associated with vaccination in a human subject in need thereof, comprising:
   administering an effective amount of a pharmaceutical composition to the subject before the subject is vaccinated, wherein the pharmaceutical composition consists essentially of:
   a) a non-steroidal anti-inflammatory drug (NSAID); and
   b) a co-agent selected from the group consisting of: fexofenadine, ketotifen, desloratadine and cetirizine and combinations thereof;
   wherein the side effects associated with the vaccination are inhibited in the human subject.

2. The method of claim 1 wherein the NSAID is selected from the group consisting of: aspirin, ibuprofen, naproxen, diclofenac, diflunisal, etodolac, indomethacin, ketoprofen, ketorolac, meloxicam, nabumetone, oxaprozin, piroxicam, salsalate, sulindac, and tolmetin.

3. The method of claim 1 wherein the NSAID is naproxen sodium and the co-agent is fexofenadine.

4. The method of claim 3 wherein the amount of naproxen sodium is about 220 mg to about 880 mg, and the amount of fexofenadine is about 60 mg to about 180 mg.

5. The method of claim 4 wherein the naproxen sodium and the fexofenadine are combined in one unit dose.

6. The method of claim 4 wherein the naproxen sodium and the fexofenadine is in the form of a tablet, lozenge or chewing gum.

7. The method of claim 1 wherein the pharmaceutical composition is administered daily beginning at most 24 hours before administration of an influenza vaccine.

8. The method of claim 1 wherein the vaccine is an influenza vaccine.

9. The method of claim 1 wherein the side effects include injection site soreness, congestion, coughing, fever, and/or muscle/joint pain.

10. The method of claim 1 wherein the amount of ibuprofen is about 200 mg to about 800 mg.

11. The method of claim 1 wherein the amount of aspirin is about 325 mg to about 1000 mg.

12. The method of claim 1 wherein the amount of ketotifen is about 0.5 mg to about 3 mg.

13. The method of claim 1 wherein the amount of desloratidine is about 5 mg to about 10 mg.

14. A method of inhibiting side effects associated with vaccination in a human subject in need thereof, comprising:
    administering an effective amount of a pharmaceutical composition to the subject within about 48 hours after the subject is vaccinated, wherein the pharmaceutical composition consists essentially of:
    a) a non-steroidal anti-inflammatory drug (NSAID); and
    b) a co-agent selected from the group consisting of: fexofenadine, ketotifen, desloratadine, cetirizine and combinations thereof;

wherein the side effects associated with the vaccination are inhibited in the human subject.

* * * * *